United States Patent
Ganciu Petcu et al.

(10) Patent No.: US 7,229,589 B2
(45) Date of Patent: Jun. 12, 2007

(54) METHOD FOR DECONTAMINATION

(75) Inventors: Mihaï Ganciu Petcu, Bucharest (RO);
Anne-Marie Pointu, Paris (FR);
Bernard Legendre, Chatenay-Malabry (FR); Johannes Orphal, Massy (FR);
Michel Vervloet, Bures-sur-Yvette (FR); Michel Touzeau, Orsay (FR);
Najet Yagoubi, Choisy-le-Roi (FR)

(73) Assignees: Centre National de la Recherche Scientifique--CNRS, Paris (FR);
Universite Paris Sud(Paris 11), Orsay Cedex (FR)

( * ) Notice: Subject to any disclaimer, the term of this patent is extended or adjusted under 35 U.S.C. 154(b) by 643 days.

(21) Appl. No.: 10/610,158

(22) Filed: Jun. 30, 2003

(65) Prior Publication Data

US 2004/0265166 A1    Dec. 30, 2004

(51) Int. Cl.
*A61L 2/00*    (2006.01)
(52) U.S. Cl. .................. 422/22; 250/455.11; 422/1; 422/23; 422/121
(58) Field of Classification Search .............. 422/22, 422/1, 23, 121; 250/455.11
See application file for complete search history.

(56) References Cited

U.S. PATENT DOCUMENTS 3,383,163 A    5/1968   Menashi
5,200,158 A    4/1993   Jacob
6,030,506 A    2/2000   Bittenson et al.
6,345,497 B1   2/2002   Penetrante

FOREIGN PATENT DOCUMENTS

FR    2 790 962 A1    9/2000
FR    2 821 557 A1    9/2002

OTHER PUBLICATIONS

"Remote plasma-enhanced chemical vapour deposition of silicon nitride at atmospheric pressure", Nowling et al., Plasma Sources Sci. Technol. 11, Feb. 4, 2002.
"Generation of Large-Volume, Atmospheric-Pressure, Nonequilibrium Plasmas" IEEE Transactions on Plasma Science, vol. 38, No. 1, Feb. 2000.
"GTP 81 Over atmospheric pressure flowing afterglow", proceeding of GEC 2002, Minneapolis, Oct. 2002.
Soloshenko, "Sterilisation of Medical Products in low Pressure Glow-Discharges", Plasma Physics Reports, vol. 26, n 9, 2000, pp. 792-800.
Written Opinion of International Searching Authority for PCT Application No. PCT/EP2004/007995.
International Search Report PCT/EP2004/007995; report dated Nov. 23, 2004.

*Primary Examiner*—Krisanne Jastrzab
(74) *Attorney, Agent, or Firm*—Marshall, Gerstein & Borun LLP

(57) ABSTRACT

A method for decontamination of a contaminated region containing biological species to be destroyed, includes a decontamination step during which a decontamination gas containing atomic nitrogen is propagated in the contaminated region, and atomic nitrogen contributes to the destruction of biological species in the contaminated region.

14 Claims, 2 Drawing Sheets

METHOD FOR DECONTAMINATION

FIELD OF THE INVENTION

The present invention is related to a method for decontamination.

BACKGROUND OF THE INVENTION

Decontamination is performed in a wide range of ways, depending for example of the nature of the object to be decontaminated. In hospitals, for instance, the validated method for sterilization uses sealed autoclaves, at temperatures over 373K. Nevertheless, these temperatures can be harmful to those non-metallic materials which make up at least part of the objects to be decontaminated.

In another proposed decontamination/sterilization method, disclosed in FR-A-2 790 962, an active species having sporicidal effect is obtained from a mixture of $H_2O$, $N_2$ and $O_2$ and is transported in a region to be decontaminated. In this method, nevertheless, the use of water vapour in the decontaminating gas can cause the production of acid, which can be harmful to the materials to be decontaminated.

In the proceedings of club PISE "Stérilisation d' instruments médicaux par plasmas froids" ("Sterilization of medical apparatus by cold plasmas"), published Oct. $19^{th}$, 2001, it is described, in "Post décharge en écoulement dans des tubes à la pression atmosphérique" ("Post-discharge in tubes at atmospheric pressure") an experiment wherein a discharge is created in a gas containing $N_2$ and $O_2$ and the afterglowing activated gas is propagated in a tube and exhibits UV fluorescence in an optical region that might be useful for decontamination. Nevertheless, the active species in this experiment is unknown and, would decontamination be provided by such a method, it would still be necessary to assess its potential effect on the materials of the decontamination area.

OBJECTS AND SUMMARY OF THE INVENTION

It is therefore an object of the present invention to provide an efficient decontamination method which could be harmless to the materials to be decontaminated.

To this end, the present invention provides a method for decontamination of a contaminated region containing at least biological species to be destroyed, comprising a decontamination step during which a decontamination gas containing at least atomic nitrogen is propagated in said contaminated region, and said atomic nitrogen contributes to the destruction of at least part of said biological species in said contaminated region.

Such biological species include for example cells, spores, bacteria, and others.

Nitrogen being dry, non-corrosive and not contributing to production of acid, it is therefore benign to most materials.

In various embodiments of the invention, one may use one and/or other of the following features:

the method further comprises an activation step, during which said decontamination gas is obtained by dissociation in a generator of a source gas containing molecular nitrogen at a pressure between 50 and 4,000 Torr;

the method further comprises a generation step wherein said source gas is generated by a source gas generator adapted to produce, from atmospheric air, a source gas containing at least 99% $N_2$ in volume;

said source gas contains over 99% $N_2$ in volume, and preferably over 99.95%;

said decontamination region is inside a decontamination enclosure comprising an intake end and an exhaust end, and a vector gas is propagated into said decontamination enclosure from said intake end to said exhaust end;

said decontamination gas is propagated into said decontamination enclosure in the vicinity of said intake end;

during activation step, source gas is partly dissociated into at least atomic nitrogen and molecular nitrogen forming at least part of said vector gas;

said exhaust end is in communication with atmospheric air;

exhaust gas is collected in said exhaust end and is fed back to form at least part of vector gas;

vector gas comprises at least a gas taken among $O_2$ and air;

said source gas flows into the generator at a given flow rate and, during activation step, said source gas is passed between two electrodes and is dissociated by discharge voltage applied at a given discharge frequency between said two electrodes, each discharge following a given discharge path between said two electrodes, said discharge frequency being adapted to said flow rate so that subsequent discharge paths are independent with respect to each other;

said decontamination gas is propagated in said contaminated region so that decontamination gas temperature is comprised between 220 and 400 K in said contaminated region;

at the exhaust end, said decontamination gas contains decontamination products and said decontamination products are filtered out of decontamination gas to provide for a cleaned decontamination gas;

the method further comprises an input step wherein said source gas fed into said generator has at least one of the following characteristics:
a flow speed comprised between 1 and 100 m/s, and
a temperature comprised between 220 and 400 K and,
during activation step, said discharge frequency is comprised between 1 kHz and 200 kHz.

According to another aspect, the invention provides a method for decontamination of a contaminated sample comprising a placing step wherein said contaminated sample is placed within said decontamination enclosure.

According to still another aspect, the invention provides a method for decontamination of a duct, said duct comprising contaminated internal walls and at least a first and a second duct openings, wherein said first duct opening forms said intake end, said second duct opening forms said exhaust end, and wherein said internal walls form said decontamination enclosure, said decontamination gas being propagated from at least one duct opening.

In another embodiment, one may use the following feature:

said duct contains further openings, and said method comprises a setting step wherein said further openings are either sealed, connected to a generator, or provided with a filter.

BRIEF DESCRIPTION OF THE DRAWINGS

Other features of the invention will become apparent with the following detailed description of several embodiments thereof, illustrated by the accompanying drawings, in which.

On the various figures, similar or identical features are designated by the same numeral references.

MORE DETAILED DESCRIPTION

Figure 1:
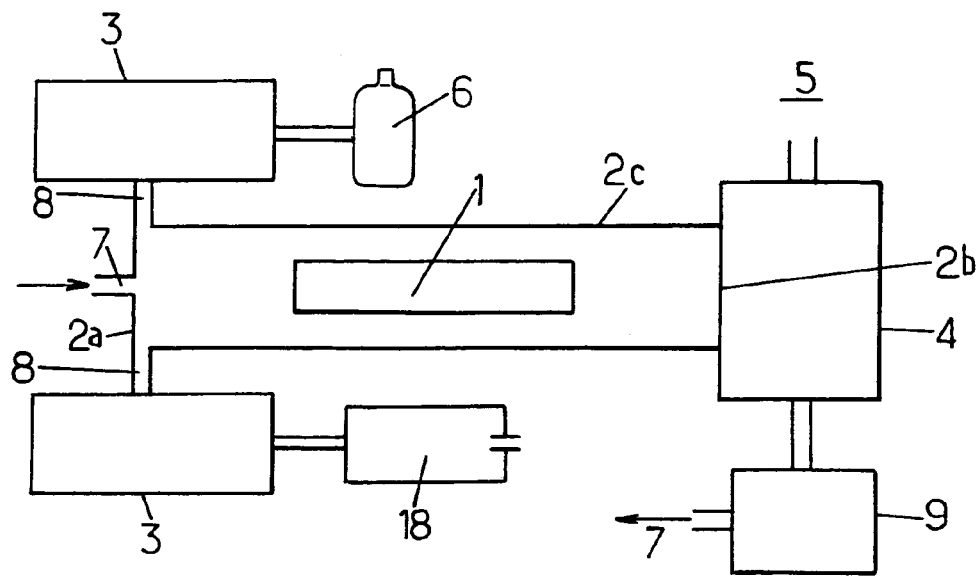
FIG. 1 is a schematic view of a decontamination apparatus according to a $1^{st}$ embodiment of the invention.
Figure 2:
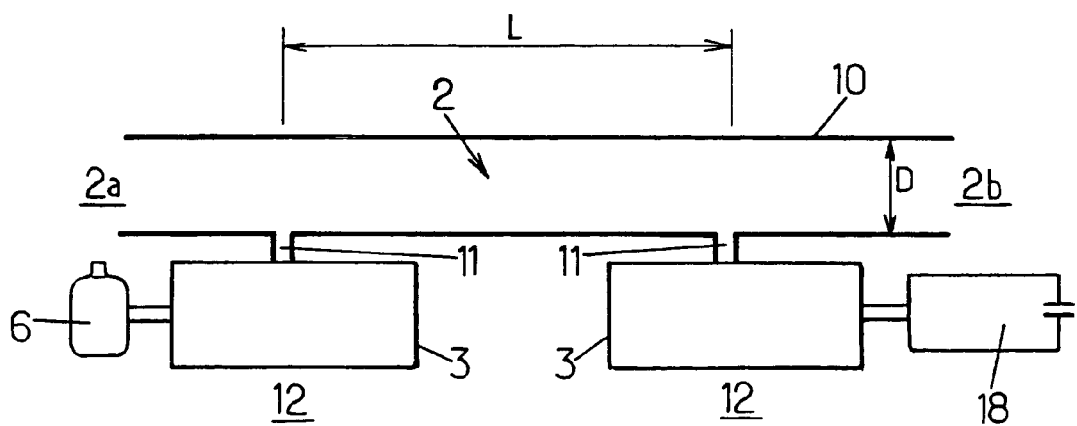
FIG. 2 is a schematic view of a decontamination apparatus according to a second embodiment of the invention.

FIG. 1 represents a first application of the inventive method to decontamination of contaminated samples. Such samples can for example be medical apparatus too expensive to be discarded after a single utilisation, e.g. implants, endoscopes, catheters and similar small dimensions apparatus. The contaminated sample is not necessarily of medical type, and could for example be material used in food industry, papers, archaeological materials, or other suitable materials. Some particularly well-suited samples are those samples with intricate surface designs for which state of the art techniques do not prove efficient, like for example syringes.

By decontamination is understood here a destruction of biological species, such as cells, spores, bacteria, virus, micro-organisms, prions, fungus or others, most often deposited on the surface of the contaminated samples. Such decontamination can for example be a step in a sterilization process, or even a sterilization process on its own. Indeed, the imperative sporicidal effect for a sterilization process of achieving reduction of the concentration of bacteria by 12 decades can be achieved by the inventive method.

Figure 3A:
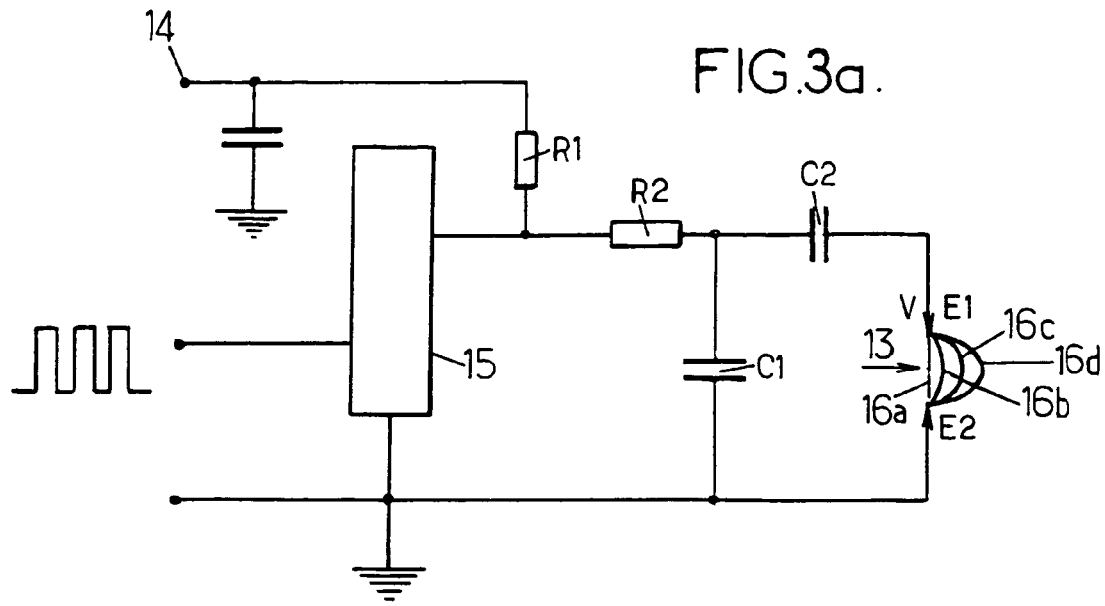
FIG. 3a is a schematic view of an atomic nitrogen generator according to the invention.
Figure 3B:
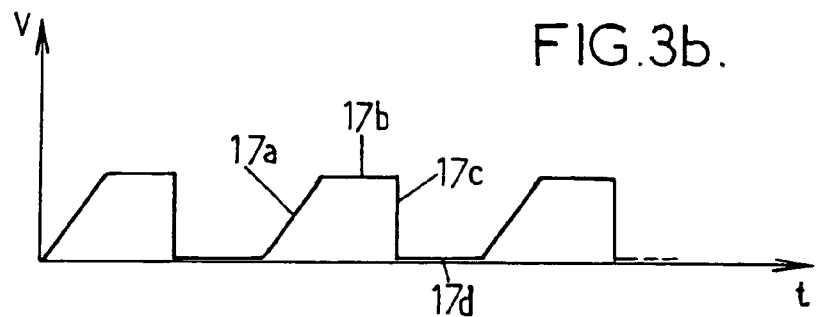
FIG. 3b is a diagrammatic view of voltage pulses used in the generator, according to the invention.
Figure 3C:
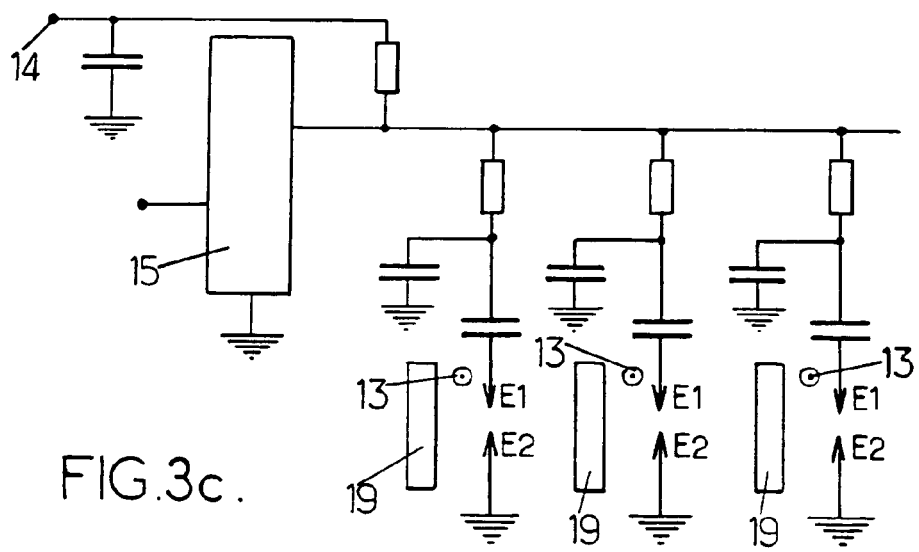
FIG. 3c is a schematic view of an atomic nitrogen generator according to the invention.

The contaminated sample 1 is placed in an adapted decontamination enclosure, for example cylindrical or hexahedral and of large enough dimensions to hold sample 1. Such a decontamination enclosure could for example consist of a one meter long and 20 cm wide cylindrical wall $2c$, these dimensions being purely illustrative, ending on each side by respective first and second ends $2a$, $2b$. The internal wall of the decontamination enclosure is made of any suitable material such as glass, plastics, ceramics, metals or others. On first end $2a$, the decontamination enclosure is connected to at least one atomic nitrogen generator 3 via an entrance duct 8. Such atomic nitrogen generator can for example be of the kind illustrated hereinafter with respect to FIG. 3, or any other suitable generator. On second end $2b$, hereinafter referred to as exhaust end, the decontamination enclosure can for example be open to the ambient air 5, optionally through a filter 4 adapted to filter out the eventual products of the decontamination. The inside of said decontamination enclosure defines a contaminated space, with a high concentration of biological species to be destroyed.

Each generator can be connected to a source of gas 6 that emits a flow of gas containing gaseous molecular nitrogen towards the generator. The source gas can for example flow at around 500 cm$^3$/s. In addition to N$_2$, the source gas could for example contain other gas which have no decontamination effect but could be useful in other stages of an associated method.

N$_2$ of purity over 99% can be used in the scope of the present invention. Such N$_2$ is for example provided by a nitrogen jar. A molecular nitrogen generator 18 can also be used to generate a source gas with a controlled volume amount of N$_2$ for example over 99.99%. Such molecular nitrogen generators 18, for example Pressure Swing Adsorption nitrogen generators such as DYF (5–23) commercialized by Rich Air Separation Co. Ltd can be used to separate nitrogen from other gases contained in the air, using two beds of Carbon Molecular Sieve (CMS).

N$_2$ purity requirements can be decreased at lower operative temperatures, which might nevertheless require other operative settings, so that a trade-off appears the best solution depending on the intended application. Operative temperature can also be raised up to around 400K, if permitted by the decontaminated sample, so that decontamination properties of heat are added to the inventive method.

The source gas flows into the generator(s) 3 in which the gas is dissociated to provide nitrogen atoms such as N($^4$S), N($^2$D) and N($^2$P). Dissociation can for example occur under ambient conditions of temperature and pressure. If the contaminated sample 1 is made of thermo-sensible material, or for any other appropriate reason, the temperature of the gas in the generator can be kept under 373K at close-to-atmospheric pressure. The pressure of the vector gas can be adapted depending of the operative needs, in the range 50–4,000 Torr for example.

As a result of the dissociation process in the generator 3, the flow of gas entering the contaminated region contains atomic nitrogen, for example in concentrations around $10^{14}$ cm$^{-3}$ to $10^{15}$ cm$^{-3}$. This concentration decreases with the distance z from the generator. At atmospheric pressure, vector gas temperature of 300K and purity of N$_2$ over 99.99%, the concentration [N] of atomic nitrogen as a function of z could be roughly described by following equation:

$$1/[N]=1/[N_0]+k \cdot z,$$

where z is in centimeters, [N$_0$] the concentration of atomic nitrogen close to the generator, and k is a constant depending on the flow of gas. Typical k values could be found between $10^{-17}$ and $10^{-15}$ cm$^2$. Thus, high atomic nitrogen concentrations are maintained in the whole contaminated region.

The first end $2a$ of the decontamination enclosure optionally contains an intake duct 7 for a vector gas, which could for example flow at around 20 m/s into the decontamination enclosure, in a way that the vector gas intake duct 7 is close enough to the entrance ducts 8 through which decontamination gas enters contaminated region, in order for the vector gas to carry efficiently the decontamination gas throughout the contaminated region. Flow speed might range approximately between 1 m/s, which makes it possible for the active species to reach intricate parts of the contaminated sample 1, and 100 m/s, which makes it possible to keep high decontamination efficiency even far away from the intake.

Vector gas can for example be pure N$_2$, optionally the same gas as provided by the gas sources 6, or air filtered in intake duct 7 to contain no more than 0.1% O$_2$ in volume.

In addition, such gas containing O$_2$ can also be introduced into decontamination enclosure in the vicinity of contaminated sample 1. Thus, one can obtain in the decontamination enclosure species by reaction of atomic nitrogen and oxygen, such as N($^4$S), N($^2$D), N($^2$P), N$_2$(B), N$_2$(A), O($^3$P), O($^1$D), O($^1$S), O$_2$($^1\Sigma$), O$_2$($^1\Delta$), O$_3$, NO, N$_2$O, NO$_2$, NO$_3$ and N$_2$O$_5$, and UV photons.

Atomic nitrogen transports chemical energy from the generator to the contaminated sample, without significant recombination or losses on the walls of the decontamination enclosure. This energy is associated with a decontamination effect, where the nitrogen atoms and nitrogen-atom-induced species and photons come in contact with biological species of the contaminated sample 1. In some experiment, it has been shown that in some point of the contaminated region with concentration of atomic nitrogen around $10^{13}$ cm$^{-3}$, concentration of *B. stéarothermophilus* roughly decreased as a function of time t according to an exponential function of the type $e^{-t/t_o}$, where $t_o$ is of the scale of the minute. High decontamination activity is therefore obtained in the whole contaminated region, and not only close to the generators. Of course, decontamination with the inventive method is not limited to applications to *B. Stéarothermophilus*, but covers all kind of biological species to be destroyed.

Using $N_2$ as vector gas at atmospheric (or close to atmospheric) pressure and temperature enables a decontamination which has no harmful effect on the sample to be decontaminated, neither due to warmth nor to acid production. Exhaust gas arriving at the second end 2*b* of the decontamination enclosure can be filtered by an adapted filter 4, before leaving into the atmosphere, or can be fed back into the generator 3. Optionally, said exhaust gas is recycled by an adapted recycling unit 9 and fed back to intake duct 7, as shown on FIG. 1. The gas may freely exit into the atmosphere, because the vector and source gas being nitrogen, it causes no harm to the environment. The eventual amounts of —$N_yO_x$ or —$O_3$ in the exhaust can be controlled to less than a ppm. Suitable filters are already described in U.S. Pat. Nos. 6,345,497, 5,547,651, 5,782,085 and 5,640,845 for pollution control methods using atomic nitrogen, for the automotive industry.

It is possible to add many parallel generators connected to different entrance points of the first end of the contaminated region such as shown on FIG. 1, as well as a main entrance point through which a non-dissociated vector gas is fed into the decontamination region, without passing through a generator.

With reference to FIG. 2, a second embodiment of the method for decontamination is presented in which the method is used to decontaminate internal walls 10 of a contaminated region 2, in particular a room or ducts such as aeration conducts and the like. FIG. 2 accordingly represents an aeration conduct of diameter D of a few centimeters and a length L of some meters. Such ducts commonly have open sections 11 which are connected to different rooms 12 in a building. No decontamination enclosure is therefore needed, as decontamination enclosure is formed by said internal walls 10 of conducts.

Where it is possible to do so, the open sections are connected to a generator 3 of the kind used in the method described in FIG. 1. Open sections which are not connected to a generator could be left open, optionally through a filter, or are closed for the duration of the decontamination, so that a suitable gas flow rate could be maintained throughout duct 2. The vector gas is input through first end 2*a* of the aeration duct, and carries the decontamination gases output by the generators and containing the active species, throughout the duct. If necessary, decontamination gas and decontamination products are filtered in second end 2*b* of the duct, optionally recycled and fed back to first end 2*a*.

The working principles of the generator are now described with respect to the specific embodiment of FIG. 3*a* and 3*b*. Nevertheless, any generator able to produce nitrogen atoms in operative concentrations at those operative conditions is considered to be encompassed by the present document. In particular, generators described in aforementioned patents U.S. Pat. Nos. 6,345,497, 5,547,651, 5,782,085 and 5,640,845 are suitable.

In the described method, the flow of nitrogen gas in the contaminated region has the following characteristics:

- a concentration of nitrogen atoms close to generator of $10^{15}$ $cm^{-3}$,
- a flow speed of 20 m/s, vector gas pressure close to atmospheric pressure, and
- a temperature of 300 K.

The present generator is adapted to provide with such a flow. The generator comprises two electrodes, $E_1$ and $E_2$ between which source gas flows from gas sources 6 at a given flow rate, as indicated by arrow 13 on FIG. 3. A voltage pulse is periodically applied from a voltage source 14 of power between 10 and 100 W, and a fast commuter 15 for providing short pulses between the two electrodes. These shorts pulse enable an efficient breakdown of the gas with a high voltage while limiting the transferred charge. The pulse comprises a voltage increase stage 17*a*, a steady state stage 17*b*, for example around 20 kV, a voltage decrease stage 17*c*, and an off-state stage 17*d*, as shown on FIG. 3*b*. Discharge frequency rate is for example around 30 kHz, in this particular embodiment. Discharge frequency and gas velocities are adapted to each other so that subsequent discharges are temporally independent with respect to each other.

If the voltage increase stage 17*a* occurs during a very short time, many energetic electrons will be produced in the gas which will be effective for molecular nitrogen dissociation and atomic nitrogen production. Nevertheless, if one increases the frequency rate at which such increase stages occur, rest species from the precedent discharge would still be present between the electrodes, the necessary voltage to be applied for the dissociation will decrease, which in turn will decrease the discharge efficiency.

A solution is to have an adapted gas flow between the electrodes, so that rest species are carried away with the non-activated species. Each pulse creates an ionisation path between the two electrodes which is subsequently moved with the gas.

A first discharge will thus follow a straight path 16*a* between the electrodes. With the gas flowing in the direction of arrow 13, the rest species of first discharge will be located around 16*b* when second discharge occurs. Path 16*b* will therefore be a preferential path for second discharge, as well as paths 16*c* and 16*d* for subsequent discharges. Each time, the spatial extent of the discharge is longer, and the voltage necessary for gas breakdown will decrease, therefore having a negative effect on dissociation efficiency.

This phenomenon will continue until the ionised path from the precedent discharge is too far away and the discharge follows a new ionisation path straight between the two electrodes that maximises the voltage. If the gas flow rate is adapted, the path ionised by the first pulse is already "too far away" from the electrodes when the second pulse occurs, so that maximal voltage is obtained for all discharges.

Furthermore, screens can be placed between the electrodes in order to provide for spatial independence of the discharges, such as shown on FIG. 3*c*, where gas flows normal to the plane of the Figure as indicated by arrow 13 pointing towards us. Isolating screens 19, made from glass or ceramics, for example, separate many dissociation entities such as described previously with respect to FIG. 3*a*, so that discharges can take place independently.

Such discharge electrodes can readily be set in series or in parallel in the gas flow in order to provide for efficient nitrogen dissociation.

Such generators offer the following advantages:

- fast pick-up by vector gas, enabled by the small volume of atomic nitrogen generation region,
- generators easily set in series or parallel, ability to provide wide operative temperature and pressure ranges, ability to cool vector gas by expansion after 4the discharge, high reliability, performance comparable to beam electron techniques for lower costs, reduced electromagnetic noise.

In the method presented here, the atomic nitrogen high concentrations are obtained in the post-discharge of a nitrogen plasma, but any classical way of obtaining high nitrogen atom concentrations such as electron beam techniques, micro-waves or sparks, offering suitable atomic nitrogen concentrations gas flow rate and speeds at operative temperature and pressure could alternatively be used within the method.

We claim:

1. Method for decontamination of a contaminated region containing at least biological species to be destroyed, comprising an input step wherein a source gas containing molecular nitrogen at a pressure between 50 and 4,000 Torr is flown into a generator at a given flow rate, said method further comprising an activation step, during which said source gas is passed between two electrodes of said generator and is dissociated by a discharge pulse applied at a given discharge frequency between said two electrodes, each discharge pulse following a given discharge path adapted to said flow rate so that subsequent discharge paths are independent with respect to one another, thereby producing a decontamination gas, said method further comprising a decontamination step during which said decontamination gas containing at least atomic nitrogen is propagated from said generator into said contaminated region, so that a decontamination gas temperature is comprised between 220 K and 400 K in said decontamination region, and said atomic nitrogen contributes to the deconstruction of at least part of said biological species in said contaminated region.

2. Method according to claim 1 comprising a generation step, wherein said source gas is generated by a source gas generator adapted to produce, from atmospheric air, a source gas containing at least 99% $N_2$ in volume.

3. Method according to claim 1, wherein said source gas contains over 99% $N_2$ in volume.

4. Method according to claim 1 wherein said decontamination region is inside a decontamination enclosure comprising an intake end and an exhaust end, and wherein a vector gas carrying said decontamination gas into said contaminated region is propagated into said decontamination enclosure from said intake end toward said exhaust end.

5. Method according to claim 4, wherein said decontamination gas is propagated into said decontamination enclosure adjacent said intake end.

6. Method according to claim 4, wherein during said activation step, source gas is partly dissociated into at least atomic nitrogen and molecular nitrogen forming at least part of said vector gas.

7. Method according to claim 4, wherein said exhaust end is in communication with atmospheric air.

8. Method according to claim 4, wherein said exhaust gas is collected in said exhaust end and is fed back to form at least part of vector gas.

9. Method according to claim 4, wherein said vector gas comprises at least a gas taken among $O_2$ and air.

10. Method according to claim 4 wherein, at the exhaust end, said decontamination gas contains decontamination products and wherein said decontamination products are filtered out of said decontamination gas to provide for a cleaned decontamination gas.

11. Method according to claim 1 wherein during said input step, said source gas fed into said generator has at least one of the following characteristics:

a flow speed comprised between 1 and 100 m/s, and a temperature comprised between 220K and 400K, and wherein, during activation step, said discharge frequency is comprised between 1 kHz and 200kHz.

12. Method according to claim 4, further comprising a placing step wherein a contaminated sample is placed within said decontamination enclosure.

13. Method of claim 4, further comprising a duct, said duct comprising contaminated internal walls and at least a first and a second duct openings, wherein said first duct opening forms said intake end, said second duct opening forms said exhaust end, and wherein said internal walls form said decontamination enclosure, said decontamination gas being propagated from at lest one duct opening.

14. Method according to claim 13, said duct containing further openings, said method comprising a setting step wherein said further openings are either sealed, connected to a generator, or provided with a filter.

* * * * *

UNITED STATES PATENT AND TRADEMARK OFFICE
CERTIFICATE OF CORRECTION

PATENT NO. : 7,229,589 B2
APPLICATION NO. : 10/610158
DATED : June 12, 2007
INVENTOR(S) : Mihai G. Petcu et al.

It is certified that error appears in the above-identified patent and that said Letters Patent is hereby corrected as shown below:

At Column 8, line 40 Claim 13, "lest" should be -- least --.

Signed and Sealed this

Third Day of August, 2010

David J. Kappos
*Director of the United States Patent and Trademark Office*